United States Patent [19]

Caldwell et al.

[11] 4,289,707

[45] Sep. 15, 1981

[54] NITROGEN HETEROCYCLES

[75] Inventors: Albert G. Caldwell, West Wickham; Norman Whittaker, Beckenham, both of England

[73] Assignee: Burroughs Wellcome Co., Research Triangle Park, N.C.

[21] Appl. No.: 888,524

[22] Filed: Mar. 21, 1978

[30] Foreign Application Priority Data

Mar. 23, 1977 [GB] United Kingdom ............... 12144/77

[51] Int. Cl.$^3$ .............................................. A61K 31/23
[52] U.S. Cl. ................................. 260/404.5; 424/250; 424/385; 424/366; 260/402.5
[58] Field of Search ............................... 260/404.5 PA

[56] References Cited

U.S. PATENT DOCUMENTS 3,231,528  1/1966  McWhorter et al. ..... 260/404.5 PA
3,324,155  6/1967  Thompson et al. ....... 260/404.5 PA Primary Examiner—Donald G. Daus
Assistant Examiner—James H. Turnipseed
Attorney, Agent, or Firm—Donald Brown

[57] ABSTRACT 1,3,6-Trisubstituted piperazine-2,5-diones having biological properties related to those of the natural prostaglandins, their synthesis, compositions containing them, and their use in medicine.

7 Claims, No Drawings

NITROGEN HETEROCYCLES

This invention relates to heterocyclic compounds, their synthesis, compositions containing them, and their use in medicine.

Piperazine derivatives, defined hereinbelow in formula (I), have been found to have pharmacological properties related to those of natural prostaglandins; as demonstrated by their ability to mimic or antagonise the physiological effects of the natural prostaglandins in various biological preparations. In particular, certain compounds of formula (I) have been found to mimic the anti-platelet aggregatory properties of prostaglandin $E_1$.

In formula (I)

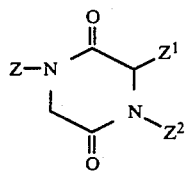

Z is hydrogen or alkyl;
one of $Z^1$ and $Z^2$ is represented by the group —$CH_2$—X—$X^1$—$X^2$
wherein X is phenylene, —C≡C—, cis or trans —CH=CH— or —$CH_2$—$CQ_2$— in which each Q is independently selected from hydrogen and alkyl such as ethyl or the two Q's together form an alkylene radical having four, five or six carbon atoms; $X^1$ is a covalent bond or a straight or branched alkylene chain having 1 to 6 carbon atoms optionally having one of its methylene groups replaced by oxa(—O—) or thia(—S—) provided that at least one carbon atom separates the oxa or thia group from a —C≡C—, —CH=CH— or —CO— group; and $X^2$ is selected from 5-tetrazolyl, carboxyl, carboxamide, hydroxymethylene and alkoxycarbonyl;
and the other of $Z^1$ and $Z^2$ is represented by the group —Y—$Y^1$—$Y^2$—$Y^3$
wherein Y is —$CR_2$—$CH_2$— in which each R is independently selected from hydrogen and methyl; $Y^1$ is carbonyl, methylene, methylene substituted by hydroxyl or methylene substituted by hydroxyl and alkyl; $Y^2$ is a covalent bond or straight or branched alkylene having 1 to 7 carbon atoms optionally substituted on the carbon adjacent $Y^1$ by one or two groups each of which may be alkyl or a cyclic radical, $Y^3$ is hydrogen, hydroxy, alkoxy having 1 to 7, preferably 1 to 4, carbon atoms, a cyclic radical, phenyl, benzyl, phenoxy or benzyloxy, wherein each of phenyl, benzyl, phenoxy and benzyloxy may be substituted in the benzene ring by one or more groups selected from hydroxy, halogeno, nitro, amino acylamino, alkenyl, alkoxy, phenyl and alkyl which may itself be substituted by one or more halogeno groups; or $Y^2$ and $Y^3$ together form an alkyl group having 1 to 7 carbon atoms of which at least one hydrogen is replaced by fluoro; or Y is a bond, —$CH_2$—, or —$CH_2$.$CH_2$— and $Y^1$, $Y^2$ and $Y^3$ taken together form a cycloalkyl or bicycloalkyl group substituted by a hydroxyl group which preferably has three carbon atoms separating it from the hydantoin ring.

In formula (I), the term cyclic radical means the monovalent radical derived by loss of a ring hydrogen atom from a monocyclic or polycyclic compound having from 3 to 12 ring atoms selected from carbon, nitrogen, oxygen, and sulphur, which compound may be saturated or unsaturated and may be further substituted by one or more alkyl groups, but excluding phenyl. Such cyclic radicals include cycloalkyl having 3 to 10 carbon atoms such as cyclopropyl, cyclopentyl, cyclohexyl and cyclooctyl, bicycloalkyl having 4 to 10 carbon atoms such as adamantyl or norbornanyl (bicyclo [2,2,1,] heptyl), spiro-alkanyl having 5 to 12 carbon atoms such as 2-spiro[3,3]heptyl, 1-spiro[4,4]nonane and 8-spiro[4,5]decane, cycloalkenyl having 4 to 10 carbon atoms such as 4-cyclopentene, heterocyclic radical such as tetrahydrofuranyl and tetrahydropyranyl and heteroaryl radicals such as thienyl, furyl, pyridyl, pyrimidyl, thiazolyl, imidazolyl and diazapinyl. Included in the term cyclic radical are those wherein one or more hydrogen atoms are replaced by fluoro.

Unless otherwise stated, in formula (I) and other formulae in this specification, alkyl moieties are selected from methyl, ethyl, propyl, butyl, pentyl and hexyl, including all isomers thereof; for example, in the definitions of $Y^1$ and $Y^2$ the alkyl groups are preferably methyl, and the alkyl moiety of alkoxycarbonyl is desirably methyl or ethyl. Similarly alkenyl groups have 2 to 4 carbon atoms for example vinyl.

In a compound of formula (I) the bonding of the divalent phenylene group may be ortho, meta or para, and the oxa or thia group is preferably adjacent the phenylene or when X is other than phenylene then $X^1$ may be —$CH_2$—O—$CH_2$— or $CH_2$—S—$CH_2$—.

Included in the meaning of compounds of formula (I) are the salts corresponding to the carboxylic acids and tetrazoles when $X^2$ is carboxyl or tetrazolyl respectively, and the salts which may also be formed when Z is hydrogen. Particularly valuable salts for medical purposes are those having a pharmaceutically acceptable cation such as ammonium or that of an alkali metal eg. sodium and potassium, an alkaline earth metal eg. calcium and magnesium, or an organic base, particualrly an amine such as ethanolamine. Salts having non-pharmaceutically acceptable cations are included within the ambit of this invention as useful intermediates to pharmaceutically acceptable salts, or the acids or esters of formula (I).

Except when there is clear indication to the contrary, formula (I) and other formulae in the specification embrace all stereoisomers represented therein. In particular such formulae include the enantiomeric forms, such mixtures as are designated racemates, and diastereoisomers.

Within formula (I) certain structural features convey particularly desirable properties on the compound in terms of for example potency, selectivity of action, physical properties or ease of synthesis. Such features include where:
a. Z is hydrogen;
b. X is —$CH_2$.$CH_2$— or —CH:CH—;
c. $X^1$ is —$C_3H_6$—, —$CH_2$.O.$CH_2$— or —$CH_2$.S.$CH_2$—;
d. $X^2$ is carboxyl or a derivative thereof;
e. Y is —$CH_2$.$CH_2$—;
f. $Y^1$ includes a hydroxyl group;
g. $Y^2$ is a bond or is alkylene substituted by a cyclic radical; and
h. $Y^3$ is hydrogen or a cyclic radical;

and preferred compounds of the present invention possess one or more of the these features.

The compounds of formula (I) may be synthesized by any method known in the art for the synthesis of analogous compounds.

For example, they may be prepared by cyclising a compound of formula (II)

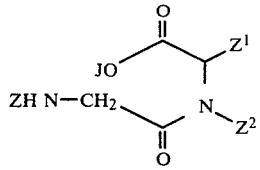

wherein Z, $Z^1$ and $Z^2$ have the same meaning as in formula (I) and J is alkyl having 1 to 6 carbon atoms, for example ethyl, which is conveniently formed in situ whence it cyclises spontaneously to provide the desired end-product.

The compound of formula (II) may be obtained from a corresponding compound of formula (III),

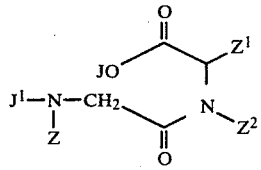

wherein Z, $Z^1$, $Z^2$ and J have the same meaning as in formula (II) and $J^1$ is a protecting group, by removal of the protecting group. Provided it is compatible with the reactants, the nature of the protecting group is not critical and may be chosen so as to be readily removed by a suitable reagent. Thus suitable meanings for $J^1$ include aryloxycarbonyl, e.g. benzyloxycarbonyl, which may be removed by an appropriate reducing agent such as by catalytic hydrogenation using a palladium-charcoal catalyst; but reductive removal of the protecting group may be inappropriate if either or both of $Z^1$ and $Z^2$ include an unsaturated bond. Alternatively, $J^1$ may be an acyl group, for example an alkanoyl group, which may conveniently be removed by hydrolysis using any method known in the art such as acid hydrolysis using a dilute mineral acid.

An intermediate of formula (III) is readily obtained by reacting a compound of formula (IV) with an ester of formula (V)

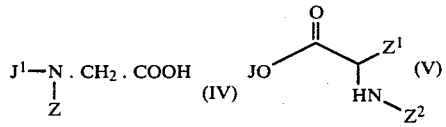

wherein Z, $Z^1$, $Z^2$, J and $J^1$ have the meaning as in formula (III). The reaction is conveniently effected in an inert solvent such as a halogenated alkane e.g. dichloromethane or chloroform, in the presence of a coupling agent such as dicyclohexylcarbodiimide. Instead of the acid of formula (IV), a corresponding reactive derivative such as an acid halide, anhydride or an activated ester, for example the ester of p-nitrophenol or thiophenol, may be used.

An intermediate of formula (V) may be conveniently prepared by reaction of a compound of formula (VI) with a compound of formula (VII):

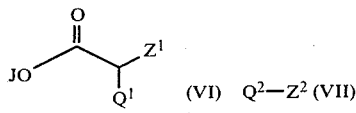

wherein J, $Z^1$ and $Z^2$ are as defined in formula (V), one of $Q^1$ and $Q^2$ is amino and the other is halogeno, preferably bromo. The reaction may be carried out be heating in the absence of solvent or in the presence of an inert solvent such as ethanol.

The intermediates of formula (V) wherein $Z^2$ is —Y—$Y^1$—$Y^2$—$Y^3$ and $Y^1$ is carbonyl may also be prepared by reaction of an amine of formula (VI) wherein $Q^1$ is amino with an unsaturated ketone of formula (VIII):

$$CR_2=CH.CO.Y^2.Y^3 \qquad (VIII)$$

wherein $Y^2$ and $Y^3$ have the same meaning as in formula (V), optionally at room temperature in the absence of solvent or by heating in the presence of an inert solvent.

Intermediates of formula (IV) are either known or can be readily obtained by the adaptation of standard chemical techniques.

In the above described synthetic procedures, although either of the groups $Z^1$ and $Z^2$ may include a carboxyl group it may be advantageous to carry out such procedures using a corresponding ester, such as an alkyl ester in which the group $X^2$ (vide supra) is lower alkyl as previously defined, for example ethyl.

In the synthesis of piperazines of formula (I) having a hydroxyl group in a side chain it may be desirable to protect this during the course of the reaction. This may be readily effected in known manner using a protecting group such as acyl, aroyl, tetrahydropyran-2-yl, 1-ethoxyethyl or aralkyl, for example benzyl.

Removal of protecting groups may be carried out by appropriate methods know to those skilled in the art: for example an acyl group may be removed by acid or base hydrolysis, and a benzyl group by reductive cleavage.

Furthermore a ketone of formula (I) wherein $Y^1$ is carbonyl may be converted to the corresponding secondary alcohol by reduction with a suitable reducing agent, such as sodium borohydride. Also, an alcohol of formula (I) wherein $Y^1$ is —CH.OH— may be oxidised to the corresponding ketone using Jones' reagent, acid dichromate or any other suitable reagent.

Similarly where the compounds of formula (I) have a C≡C or CH=CH bond these may be converted by conventional hydrogenation techniques, for example using a Lindlar type or Adams catalyst, to the corresponding ethylenic or unsaturated compounds as appropriate.

The compounds of formula (I) have an asymmetric 5-carbon atom, and a further asymmetric centre is present in those compounds wherein $Y^1$ includes a hydroxyl group. Such alcohols therefore exist as four isomers which are separable by thin layer chromatography or high performance liquid chromatography into two diastereomers, each of which is a racemic mixture of two isomers. On separation of the diastereomers, one diastereomer may be converted to a mixture of the four isomers by treatment with a base, such as an alkali metal hydroxide, and subsequently re-separated to provide two diastereomers. Repeated use of this technique enables the effectual conversion of one diastereomer to the other; this may be desirable when one diastereomer has a biological activity preferred to the other.

The corresponding alcohols of formula (III) also exist in four isomeric forms. If desired, these may be separated into two epimers and subsequent cyclisation to a compound of formula (I) retains the stereochemical configuration.

In all of the foregoing chemical procedures it is of course evident that the choice of reactant will be dictated in part by the functional groups present in the substrate, and where necessary reactants having an appropriate selectivity of action must be used.

The compounds of formula (I) are of value in having pharmacological properties related to those of natural prostaglandins that is, they mimic or antagonise the biological effects of members of the prostagladin (PG) 'A', 'B', 'C', 'D', 'E', and 'F' series. For example, compounds of formula (I) and in particular 6-(6-carboxyhexyl)-1-(3-hydroxyoctyl)piperazine-2,5-dione, have been found to mimic the antiaggregatory effect of $PGE_1$ on blood platelets, and to antagonise the contraction induced by $PGE_2$ or $PGF_2$ on smooth muscle taken from the rat stomach, rat colon, chick rectum and guinea pig trachea. In general, antagonistic properties as opposed to mimetic, have been observed when using larger doses.

The pharmacological profile, by which is meant the relative activities, mimetic or antagonistic, compared with the natural prostaglandins, will of course vary depending on the specific compound under consideration.

By reason of their prostaglandin-related properties, the compounds of formula (I) are useful in the pharmacological characterisation and differentiation of the biological activities of the natural prostaglandins and their 'receptors'. The further understanding of the physiological role of prostaglandins is of course valuable in the search for new and improved therapeutic substances.

The compounds of formula (I) are also of value as therapeutic agents. In particular compounds such as those described previously as having a potent antiaggregatory effect on blood platelets are useful whenever it is desired to inhibit platelet aggregation or to reduce the adhesive character of platelets, and may be used to treat or prevent the formation of thrombi in mammals, including man. For example, the compounds are useful in the treatment and prevention of myocardial infarcts, to treat and prevent thrombosis, to promote patency of vascular grafts following surgery, and to treat complications of arteriosclerosis and conditions such as atherosclerosis, blood clotting defects due to lipermia, and other clinical conditions in which the underlying aetiology is associated with lipid imbalance or hyperlipidemia. A further use for such compounds is as an additivie to blood and other fluids which are used in artificial extra-coporeal circulation and perfusion of isolated body portions.

Compounds of formula (I) cause relaxation of cascular smooth muscle in a similar way as do members of the prostaglandin 'A' and 'E' series. Such compounds are capable of inducing vasodilation and therefore have antihypertensive properties and are useful in lowering blood pressure in mammals, including man, and may be used alone or in combination with a β-adrenoceptor blocking agent or another antihypertensive substance for the treatment of all grades of hypertension including essential, malignant and secondary hypertension.

Compounds of formula (I) which mimic the effect of $PGE_1$ of antagonising histamine induced broncho-constriction may be used in the treatment or prophylaxis of bronchial asthma and bronchitis by alleviating the bronchoconstriction associated with these conditions.

The compounds of formula (I) which inhibit pentagastrin-induced gastric acid secretion and reduce the formation or aspirin-induced gastric lesions in rats are useful in reducing excessive gastric secretion, reducing and avoiding gastro-intestinal ulcer formation and accelerating the healing of such ulcers already present in the gastrointestinal tract whether such ulcers arise spontaneously or as a component of polyglandular adenoma syndromes.

A further utility for compounds of formula (I) is as diuretic agents, arising from the ability of intravenous infusions to dogs of such compounds to increase the urine volume. The uses of diuretic agents include the treatment of oedema for example oedema associated with heart failure, liver failure or kidney failure in man or other mammals.

A further use for compounds of formula (I) which mimic the uterine smooth muscle effects of $PGE_2$ and $PGF_{2\alpha}$ is as antifertility agents, in particular as abortifacients.

In addition compounds of formula (I) may be used in the treatment of proliferative skin diseases such as are associated with excessive cell division in the epidermis or dermis which may be accompanied by incomplete cell differentiation. Particular conditions which may be alleviated include psoriasis, atopic dermatitis, non-specific dermatitis, primary irritant contact dermititis, allergic contact dermatitis, basal and squamous cell carcinomas of the skin, lamellar icthyosis, epidermolytic hyperkeratosis, permalignant sun induced keratosis, non malignant keratosis, acne and seborrheic dermatitis in humans and atopic dermatitis and mange in domestic animals. For the treatment of these conditions the compounds are desirably applied topically to the affected skin. Alternatively they may be administered by intradermal or intramuscular injection which may be directly into the skin lesion or into the surrounding tissue. Injectable compositions will generally contain from 0.1 to 0.5% w/v of active ingredient.

The amount of a compound of formula (I) required to achieve the desired biological effect will of course depend on a number of factors, for example, the specific compound chosen, the use for which it is intended, the mode of administration, and the recipient. In general, a daily dose may be expected to lie in the range of from 1 μg to 20 mg per kilogram bodyweight. For example, an intravenous dose may lie in the range of from 5 μg to 1 mg/kg which may conveniently be administered as an infusion of from 0.01 to 50 μg per kilogram per minute. Infusion fluids suitable for this purpose may contain from 0.001 to 100, for example from 0.01 to 10, μg per milliliter. Unit doses may contain from 10 μg to 100 mg of a compound of formula (I), for example ampoules for injection may contain from 0.01 to 1 mg, and orally administrable unit dose formulations such as tablets or capsules may contain from 0.1 to 50, for example 2 to 20, mg.

More specifically, when a compound of formula (I) is used to inhibit platelet aggregation it is generally desirable to achieve a concentration in the appropriate liquid, whether it be the blood of a patient or a perfusion fluid, of about 1 μg to 10 mg, for example from the 10 μg to 1 mg, per liter.

The abovementioned doses refer to the acids, amides, esters, alcohols and tetrazoles of formula (I); where a salt is used, the dose should be taken as referring to the corresponding anion.

For use in the treatment or prophylaxis of the conditions referred to above, while the compounds may be used as the raw chemical they are preferably presented with an acceptable carrier therefor as a pharmaceutical formulation. The carrier must of course be 'acceptable' in the sense of being compatible with the other ingredients of the formulation and not deleterious to the recipient thereof. The carrier may be a solid or a liquid, and is preferably formulated with a compound as a unit-dose formulation, for example a tablet, which may contain from 0.05% to 95% by weight of the compound. Other pharmacologically active substances may also be present in formulations of the present invention as indicated above. The compounds may be incorporated in the formulations either in the form of the acid or the salt or ester thereof, and the formulations may be prepared by any of the well-known techniques of pharmacy consisting essentially of admixture of the components of the formulation.

The formulations include those suitable for oral, rectal, topical (buccal - eg. sub-lingual), the parenteral (that is subcutaneous, intramuscular and intravenous) administration, although the most suitable route in any given case will depend on the nature and severity of the condition being treated, and on the nature of the compound.

Formulations suitable for oral administration may be presented as discrete units such as capsules, cachets, lozenges or tablets each contaning a predetermined amount of compound; as a powder or granules as a solution or a suspension in an aqueous liquid or a non-aqueous liquid; as an oil-in-water emulsion; or as a water-in oil liquid emulsion. Such formulations may be prepared by any of the methods of pharmacy but all methods include the step of bringing into association the compound with the carrier which constitutes one or more accessory ingredients. In general they are prepared by uniformly and intimately admixing the compound with liquid or finely divided solid carriers or both, and then, if necessary, shaping the product into the desired presentation. For example a tablet may be prepared by compression or moulding a powder or granule of the compound, optionally with one or more accessory ingredients. Compressed tablets may be prepared by compressing, in a suitable machine, the compound in a free-flowing form such as a powder or granules optionally mixed with a binder, lubricant, inert diluent, surface active or dispersing agent(s). Moulded tablets may be made by moulding in a suitable machine the powdered compound moistened with an inert liquid diluent.

Formulations suitable for buccal (sub-lingual) administration include lozenges comprising a compound in a flavoured basis, usually sucrose and acacia or tragacanth; and pastilles comprising a compound in an inert basis such as gelatin and glycerin; or sucrose and acacia.

Formulations suitable for topical application to the skin preferably take the form of an ointment, cream, lotion, paste, gel, spray, aerosol, or oil. Carriers, which may be used include vasoline, lanoline, polyethylene glycols, alcohols and combinations thereof. The active ingredient is generally present in a concentration of from 0.1 to 15% w/w of the composition, for example from about 0.5 to about 2%.

Formulations of the present invention suitable for parenteral administration conveniently comprise sterile aqueous preparations of a compound, which preparations are preferably isotonic with the blood of the intended recipient. These preparations are preferably administered intravenously, although administration may also be effected by means of subcutaneous or intramuscular injection. Such preparations may be conveniently prepared by admixing the compound with water and rendering the product sterile and isotonic with the blood.

Formulations suitable for rectal administration are preferably presented as unit-dose suppositories. These may be prepared by admixture of the compound with one or more of the conventional solid carriers, for example cocoa butter, and shaping of the resulting mixture.

It will be appreciated from the foregoing that what we will claim may comprise any novel feature described herein, principally and not exclusively, for example:

(a) The novel compounds of formula (I) as hereinabove defined.

(b) A method for the preparation of the novel compounds of formula (I) as hereinabove described.

(c) A pharmaceutical formulation comprising a compound of formula (I) in association with a pharmaceutically acceptable carrier therefor, and methods for the preparation of such formulations.

(d) A method for lowering blood pressure in a mammal including man which comprises administration to the mammal of an effective hypotensive, non-toxic amount of a compound of formula (I).

(e) A method for the treatment or prophylaxis of thrombosis in a mammal or mammalian tissue, including human, which comprises administration of a non-toxic, effective anti-thrombotic amount of a compound of formula (I).

(f) A method for inducing vasodilation in a mammal, including man, comprising administration to said mammal of a non-toxic effective vasodilatory amount of a compound of formula (I).

(g) A method for the treatment or prophylaxis of gastric lesions in a mammal including man comprising administration to said mammal of a non-toxic effective prophylactic or therapeutic amount of a compound of formula (I).

(h) A method for inducing bronchodilation in a mammal, including man, comprising administration to said mammal of a non-toxic, effective bronchodilatory amount of a compound of formula (I).

(i) A method for the treatment or prophylaxis of an allergic condition in a mammal, including man, comprising administration to said mammal of a non-toxic effective prophlactic or therapeutic amount of a compound of formula (I).

(j) A method of inducing abortion of a foetus in a mammal including human comprising administration to said mammal of a non-toxic effective abortifacient amount of a compound of formula (I).

(k) A method of inducing infertility in a mammal including human comprising administration to said mamal of a non-toxic effective contraceptive amount of a compound of formula (I).

(1) A compound of formula (II), (III) or (V), as hereinbefore defined and hereinafter exemplified.

The following Examples are provided to illustrate the present invention but are not to be construed as a limitation thereof.

EXAMPLE 1

Preparation of 1-(6-carboxyhexyl)-6-octyl piperazine-2,5-dione

A. 2-Aminodecanoic acid (J. Am. Chem. Soc., 1946, 68 450) (16.0 g.) was added in portions to a cooled (−10° C.) mixture of absolute ethanol (70 ml.) and thionyl chloride (6 ml.) with stirring. The resulting solution was set aside for 2 h., at room temperature, refluxed for 1 h., cooled, poured into ice-water, and the pH of the solution was adjusted to 9 with aqueous sodium hydroxide. The mixture was extracted with ether, the extract was dried, concentrated, then distilled, giving ethyl 2-aminodecanoate (75%) as a colourless oil, b.p. 82°–4° C./0.2 mm.

A solution of the above aminoester (18 g.) and ethyl 7-bromoheptanoate (20 g.) in absolute ethanol (50 ml) was refluxed for 24 h., and the ethanol was then evaporated. Addition of ether precipitated a hydrobromide salt, m.p. 98° C., which was dissolved in a little dichloromethane, treated with an equivalent of triethylamine, washed thoroughly, with water, and dried; removal of the solvent gave ethyl 2-(6-ethoxycarbonylhexylamino)decanoate (52%) as a colourless viscous oil, b.p. 142°–4°/0.001 mm.

B. A solution of ethyl 2-(6-ethoxycarbonylhexylamino) decanoate (4.96 g) and benzyloxycarbonylglycine (2.8 g) in dichloromethane (30 ml) was cooled in ice and stirred during the grandual addition of dicyclohexylcarbodiimide (2.76 g). The mixture was stirred at room temperature for 2 hours, after which the solid was filtered off and the filtrate was evaporated to dryness to give ethyl 2-(N-(benzyloxycarbonylglycyl)-N-6-ethoxycarbonylhexyl)amino) decanoate as a colourless oil (8.16 g).

C. This material was cyclised to the desired piperazine via ethyl 2-(N-glycyl-N-6-ethoxycarbonylhexyl)amino decanoate by the following procedure.

To a solution of the material in ethanol (36 ml) and glacial acetic acid (4 ml) was added 10% palladium-charcoal catalyst (800 mg) and the mixture was stirred during the passage of a stream of hydrogen until the emerging gases produced no further precipitation when passed into barium hydroxide solution. The catalyst was filtered off, the ethanol was evaporated, water was added and the solution was made slightly alkaline by addition of dilute sodium hydroxide solution. The insoluble oil was extracted with ether, and the ether extract was washed with water, dried and evaporated, leaving 1-(6-ethoxy-carbonylhexyl)-6-octylpiperazine-2,5-dione, a slightly yellow oil.

A solution of the foregoing ester in ethanol (32 ml) and 2-N-sodium hydroxide (16 ml) was allowed to stand at room temperature for 1 hour. The ethanol was evaporated, water was added, the aqueous solution was washed with ether, and then acidified with 2N-hydrochloric acid. The precipitated solid was collected and recrystallised from aqueous methanol to give small colourless plates m.p. 103°–104° C.

EXAMPLE 2

Preparation of 6-(6-carboxyhexyl)-1-octylpiperazine 2,5-dione

By a series of reactions analogous to that described in Example 1, diethylaminononanedioate was converted to diethyl 2-octylaminononanedioate and thence via diethyl 2-(N-benzyloxycarbonylglycyl-N-octyl)amino)-nonanedioate and diethyl 2-(N-glycyl-N-octyl)amino)-nonanedioate to the desired 6-(6-carboxyhexyl)-1-octyl-piperazine-2,5-dione which appeared as small colourless needles m.p. 112°–115° C.

EXAMPLE 3

Preparation of 6-(6-carboxyhexyl)-1-(3-hydroxy octyl) piperazine-2,5-dione

A. Diethyl acetamidomalonate (16.7 g) and ethyl 7-bromoheptanoate (16.6 g) were dissolved in ethanolic ethoxide (prepared from sodium (1.51 g) and absolute ethanol (30 ml) and the mixture was refluxed for 27 h. The cooled solution was poured into ice-water, the product was extracted into ether, and the dried extract was evaporated to give crude diethyl acetamido-(6-ethoxy-carbonylhexyl)malonate as a pale yellow oil, 2.2(3H, singlet, -COCH$_3$), 4.17(6H, multiplet, 3×—OCH$_2$—CH$_3$). This amide was refluxed with concentrated hydrochloric acid (111 ml) for 5½ h., the cooled solution was washed with ether, and the aqueous layer was decolourised with activated charcoal and evaporated to dryness in vacuo. The residual colourless glass was dissolved in the minimum quantity of absolute ethanol and added dropwise to a stirred, cooled (−10° C.) mixture of absolute ethanol (125 ml) and thionyl chloride (15.7 g). The resulting solution was set aside at room temperature for 1 h., refluxed for 1½ h., cooled, and poured into ice-water, adjusting the pH to 9 with aqueous hydroxide. The mixture was extracted with ether, and the dried extract was concentrated and distilled, giving diethyl 2-aminononanedioate (55% yield) as a colourless oil, b.p. 114°–115°/0.02–0.03 mm.

B. Diethyl 2-aminononanedioate (10.40 g) and oct-1-en-3-one (5.04 g) were mixed slowly at 0° C., with stirring, and set aside at room temperature for 3 h., giving diethyl 2-(3-oxoctylamino) nonanedioate as a colourless oil, 2.3(4H, multiplet, —CH$_2$—CO$_2$Et and NCH$_2$CH$_2$CO—), 3.16(1H, triplet, EtO$_2$C—CHR—N), 4.11(2H, quartet, —O—CH$_2$—CH$_3$), 4.17(2H, quartet, —O—CH$_2$—CH$_3$). A stirred solution of this ketone (13.5 g) in absolute ethanol (140 ml) was treated dropwise at 0° C. with sodium borohydride (665 ml) in absolute ethanol (70 ml), then kept for 3½ h. at room temperature, and concentrated at 40° C. in vacuo. The residue dissolved in water, was brought to pH 5 with N hydrochloric acid and extracted throughly with chloroform, the extract was washed with water, dried, and evaporated, giving diethyl 2-(3-hydroxyoctylamino)nonanedioate as a colourless oil.

C. A solution of diethyl 2-(3-hydroxyoctylamino)nonanedioate (7.74 g) and benzyloxycarbonylglycine (4.6 g) in dichloromethane (90 ml) was cooled in ice and stirred during the addition of dicyclohexylcarbodiimide (4.53 g). After a further 3½ hours' stirring the precipitated dicyclohexylurea was filtered off. The filtrate was washed with 0.2 N-hydrochloric acid and then with water, dried and evaporated to leave a colourless oil (11.5 g). Chromatography of this material on a column of silica with chloroform-ethyl acetate (9:1) as eluent gave the pure diethyl 2-(N-benzyl) oxycarbonylglycyl-N-(3-hydroxyoctyl)amino)nonanedioate as a colourless oil.

This material was cyclised to the desired piperazine via diethyl 2-(N-glycyl-N-(3-hydroxyoctyl)amino)nonanedioate by the following procedure.

The oil (2.9 g) was dissolved in ethanol (26.1 ml) and glacial acetic acid (2.9 ml) and hydrogenated in the presence of 10% palladium-charcoal catalyst (580 mg) as described in Example 1, to give 6-(6-ethoxy-carbonylhexyl)-1-(3-hydroxyoctyl) piperazine-2,5-dione (1.45 g) as a colourless oil which solidified on standing, m.p. ca. 65°–80° C. (mixture of stereoisomers).

The foregoing diester (1.6 g) was stirred with a mixture of ethanol (4.8 ml) and 5 N-sodium hydroxide solution (1.2 ml) at room temperature for 1½ hours. Water was added, the aqueous solution was washed with ether, and then acidified to precipitate an oil which was extracted with chloroform. The washed and dried chloroform solution was evaporated to leave a viscous oil (1.09 g). Treatment of this oil with ether gave a colourless solid (800 mg), m.p. ca. 77°–83° C. which was a mixture of the two diastereomers of 6-(6-carboxyhexyl)-1-(3-hydroxyoctyl)piperazine-2,5-dione. The mixture was separated by means of high performance liquid chromatography on a column of silica with chloroform-methanol-acetic acid (97:2.5:0.5) as solvent to give isomer I, crystallising from ethyl acetate-light petroleum (b.p. 60°–80° C.) as colourless plates, m.p. 102°–104° C. (thin-layer chromatography on silica in chloroform-methanol-acetic acid (90:5:5) gave a single spot, Rf 0.60 and isomer II, as small colourless prisms, m.p. 102°–104° C., from ethyl acetate (thin-layer chromatography on silica in chloroform-methanol-acetic acid (90:5:5) gave a single spot, Rf 0.53).

What we claim is:

1. A compound of formula (II)

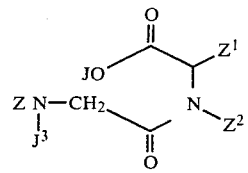

(II)

wherein J is alkyl of 1 to 6 carbon atoms, $J^3$ is hydrogen or benzyloxycarbonyl, Z is hydrogen or alkyl, one of $Z^1$ and $Z^2$ is represented by the group $-CH_2-X-X^1-X^2$ wherein X is $-CH_2-CQ_2-$ in which each Q is independently selected from hydrogen and alkyl or the two Q'S together form alkylene having from four to six carbon atoms;

$X^1$ is a covalent bond or a straight or branched alkylene chain having 1 to 6 carbon atoms;

$X^2$ is selected from carboxyl or alkoxycarbonyl; the other of $Z^1$ and $Z^2$ is represented by the group $-Y-Y^1-Y^2-Y^3$, wherein Y is $-CR_2-CH_2-$ in which each R is independently selected from hydrogen and methyl;

$Y^1$ is methylene, methylene substituted by hydroxyl or methylene substituted by hydroxyl and alkyl;

$Y^2$ is a covalent bond or straight or branched alkylene having 1 to 7 carbon atoms optionally substituted on the carbon adjacent $Y^1$ by one or two groups each of which is alkyl;

$Y^3$ is hydrogen or a salt thereof wherein the term alkyl as it appears above has one to six carbon atoms.

2. The compound ethyl 2-(N-(benzyloxycarbonylglycyl)-N-6-ethoxycarbonylhexyl amino)decanoate.

3. The compound ethyl 2-(N-glycyl-N-6-ethoxycarbonylhexyl)amino)decanoate.

4. The compound diethyl 2-(N-benzyloxycarbonylglycyl-N-(3-hydroxyoctyl)amino) nonanedioate.

5. The compound diethyl 2-(N-glycyl-N-(3-hydroxyoctyl)amino)nonanedioate.

6. The compound diethyl 2-(N-benzyloxycarbonylglycyl-N-octyl)amino)nonanedioate.

7. The compound diethyl 2-(N-glycyl-N-octyl)amino)nonanedioate.

* * * * *